(12) United States Patent
Matioc

(10) Patent No.: US 6,651,661 B2
(45) Date of Patent: Nov. 25, 2003

(54) ERGONOMIC FACE MASK

(76) Inventor: Adrian A. Matioc, 2907 Melissa Cir., Fitchburg, WI (US) 53711

( * ) Notice: Subject to any disclaimer, the term of this patent is extended or adjusted under 35 U.S.C. 154(b) by 0 days.

(21) Appl. No.: 10/096,764

(22) Filed: Mar. 12, 2002

(65) Prior Publication Data

US 2003/0172932 A1 Sep. 18, 2003

(51) Int. Cl.[7] .............................................. A62B 18/02
(52) U.S. Cl. ........................... 128/205.25; 128/205.13; 128/206.21; 128/206.22; 128/206.23; 128/206.24; 128/206.25; 128/206.26; 128/206.27; 128/206.28; 128/206.29
(58) Field of Search ..................... 128/201.24, 201.19, 128/201.12, 203.29, 205.25, 206.12, 205.13, 205.16, 207.13, 207.14, 206.13, 206.14, 206.15, 206.16, 206.18, 206.19, 206.21, 206.22, 206.23–206.29, 204.18

(56) References Cited

U.S. PATENT DOCUMENTS

| | | | | |
|---|---|---|---|---|
| 2,254,854 A | * | 9/1941 | O'Connell | 128/206.28 |
| 3,982,532 A | * | 9/1976 | Halldin et al. | 128/206.24 |
| 5,496,336 A | * | 3/1996 | Cosgrove et al. | 606/148 |
| 5,813,423 A | * | 9/1998 | Kirchgeorg | 128/202.28 |
| 6,357,437 B1 | * | 3/2002 | Jacques | 128/201.25 |

* cited by examiner

Primary Examiner—Glenn K. Dawson
Assistant Examiner—Mark A Rademacher
(74) Attorney, Agent, or Firm—Quarles & Brady LLP

(57) ABSTRACT

An ergonomic face mask is provided for the administration of gas under a positive pressure to a patient. The face mask includes a cushion that provides a seal with the patient's face, and a dome connected to the cushion that receives a connection tube for receiving the gas from a source, such as a bag. The dome is asymmetrical, and defines a plurality of grooves and protuberances configured to allow the comfortable use of the mask with one hand.

20 Claims, 6 Drawing Sheets

ERGONOMIC FACE MASK

CROSS-REFERENCE TO RELATED APPLICATIONS

STATEMENT REGARDING FEDERALLY SPONSORED RESEARCH OR DEVELOPMENT

BACKGROUND OF THE INVENTION

1. Field of the Invention

The present invention relates generally to a face mask of the type used in airway management in the anesthesiology, critical care, emergency medicine and resuscitation fields, and in particular relates to an ergonomically shaped face mask (EFM) with increased comfort and adherence to the operator's hand.

2. Description of the Related Art

The symmetrical face mask dome was first developed in the middle of the 19th century, and was designed for spontaneously breathing patients. The first face mask was designed for anesthetic purposes, whereby anesthetic gasses were administered passively through the face mask to spontaneously breathing patients in a sitting position. While the dome was sufficient for that purpose, its symmetrical nature presents challenges when providing positive pressure ventilation to a patient who isn't breathing, especially when the operator has only one hand available for the mask.

The face mask used in anesthesia, emergency medicine, critical care and resuscitation is a device through which oxygen or anesthetic gasses are administered under positive pressure to a patient. Positive pressure mask ventilation allows the forceful, active administration of oxygen and/or anesthetic gasses from a source to a non-breathing patient. Typically, the attending physician or rescuer (hereinafter collectively referred to as the operator) uses a bag-mask device and holds the face mask with the left hand and squeezes the bag (develop positive pressure air flow) with the right hand.

Several factors contribute to the success of positive pressure mask ventilation. For example, the patient's facial bone structure affects the quality of the seal between the mask and the face, it being appreciated that an unlimited variety of facial sizes and shapes exist. Accordingly, it is desirable to provide a mask that is capable of forming a reliable seal with several facial structures.

Thus, the specific design characteristics of the face mask also contribute to the success of the mask ventilation. Referring to FIG. 1, a conventional symmetrical face mask 10 is illustrated of the type used by anesthesiologists, paramedics, EMS personal, firefighters, ER personal and anybody involved in artificial ventilation. The two primary components of the face mask 10 include a cuff 11 at its base, and a symmetrical dome 22 extending upwardly from the cuff. The cuff 11 makes direct contact with the face of the patient during ventilation. The dome 22 is used by the operator to grip and seal the mask to the patient's face, and typically has a (left-right) symmetrical appearance. The dome 22 has a connector 20 for administering the gas from the source to the patient.

Thus, the ventilation technique also contributes to the success of positive pressure mask ventilation. While bag-mask ventilation is a complex technique that requires considerable skill and practice, the complexity is further increased when attempting to provide performing ventilation using one hand. A good face-mask seal is achieved by applying and corroborating two simultaneous forces. In particular, an upper pressure is applied on the dome and a lower pressure is applied to the patient's jaw. The upper forces are developed as the hand holds the mask with the thumb and index finger around the connector.

Three asymmetrical pressure areas are developed on the dome by the first and second fingers and the palm. The contact area of an operator's left hand on the mask 10 is identified generally by hatching 18. The tip of the index finger applies pressure to the right side of the dome at location 14, and the palm applies pressure to the left side of the dome at location 16. These pressure areas are connected as the left palm makes full contact with the dome (FIG. 1). The thumb engages the right side of the dome at location 12. The lower pressure forces are developed by the middle, ring, and small fingers as they pull the patient's jaw and the face mask together. The airway of a patient may be opened by applying a "jaw thrust" maneuver, which is especially critical when the patient is unconscious and the tongue obstructs the airway. If the jaw thrust maneuver is unsuccessful, the ventilation will fail regardless of the quality of seal between the mask and the patient's face.

The application of symmetrical pressure on the face mask is much more difficult when only one hand is used to position the face mask and maintain an open airway while the other hand is being used to squeeze the bag. In the example illustrated, the thumb and the tip of the index finger applies the majority of the pressure on the right side of the mask 10, while the palm and remaining fingers apply pressure to the left side of the mask. With the hand gripping the mask 10 in this position, it is apparent that a user would naturally apply asymmetrical forces to the symmetrical mask. Considering the asymmetrical forces necessary to be applied with the left hand on a symmetrical face mask, the seal is usually lost on the right side of the mask.

When using conventional face masks with one hand, the operator's hand position is therefore required to be substantially horizontal, with the wrist and forearm twisted out of their natural and relaxed position. In order to generate a sufficient grip in this position, the fingers are forced to assume a "claw-like" posture. This non-neutral position is uncomfortable, tiring, and painful especially when increased force is necessary to obtain and maintain a seal. The user also may need to change his/her grip several times, and may become fatigued, especially with sub-optimal results in ventilation. This can lead to poor oxygenation of the patient and pollution of the operating room with anesthetic gasses. Furthermore, the grip is typically realized between two smooth surfaces, in particular a gloved hand and the symmetrical dome. The situation becomes critical when secretions and blood make the smooth surfaces slippery due to face trauma, vomitus, excessive secretions, and the like.

Due to the difficulties associated with delivering positive pressure mask ventilation with one hand, the Basic Life Support (BLS) for Health Care Providers and the Guidelines 2000 for Cardiopulmonary Resuscitation- CPR and Emergency Cardiovascular Care recommend the two-rescuer use of the bag-mask. In particular, one operator is designated to properly position and hold the mask on the patient's face with two hands, while the other operator is responsible for squeezing the bag. Two hands may therefore be used in applying symmetrical pressures on the symmetrical face mask to ensure an adequate seal. However, this technique is only useful when two trained rescuers are available to manage the ventilation of the patient. In an overwhelming number of cases, however, one rescuer is forced to perform one-hand ventilation.

Improvements to positive pressure ventilation are only partially addressed by prior art. The majority of improvements made to the face mask were primarily aimed at improving the patient's comfort. As a result, face masks were produced having an inflatable and ergonomically shaped cuff that better conform to facial features, such as the chin curve. The quality of the seal between the face mask and the patient's face was still dependent upon a correct ventilation technique with the mask. The prior art fails to address the ergonomic aspect of hand-mask interaction.

For example, European patent application 0427474A2, published May 15, 1991 and entitled "Face masks and face masks components" describes a face mask and face mask components used in ventilation. In particular, a water-activated hydrophilic polyurethane foam provides a cushion to minimize discomfort to the wearer. EP 0427474 A2 acknowledges that, while face plates typically found in conventional face masks are smooth to minimize discomfort to the wearer, they do not provide a means for the user to achieve a secure grip on the mask. A thumb grip is thus provided that provides a hook for the positioning of the thumb. However, the thumb encircles the hook and does not reach maximally on the right side of the mask. As a result, the seal on the right side will be lost by poor technique. The operator will thus be forced to place the rest of the hand in a non-neutral position with twisting of the hand and the forearm so as to engage the mask in a "claw" like grip. EP 0427474 A2 does not therefore address the difficulty associated with attempting to form a tight seal by applying asymmetrical pressure onto a symmetrical face mask, and further does not address the need to establish suitable upper and lower pressures to provide a tight seal with the patient's face.

International patent publication WO 97/07847, entitled "Anesthesia Mask," discloses a symmetrical face mask is disclosed having one or more circumferential grippers located, for example, above and/or below the inlet port that is said to provide a firm grip to an operator who is dispensing anesthesia to the patient. However, not only do the grippers increase the complexity of and expense of production, WO 97/07847 disregards that a proper mask technique (e.g. upper and lower pressure) is necessary to establish a reliable seal between the mask and the patient's face. A "firm grip" on the mask does not necessarily correlate to functional upper pressure needed to produce a reliable seal with the patient's face.

WO 97/07847 discloses straps provided on the mask that are said to develop bilateral and symmetrical traction in an effort to improve the seal between the mask and the patient's face. However, the face straps only assist in developing upper pressure. Independent lower forces to pull the jaw in the mask and to realize the jaw thrust are therefore still necessary. Furthermore, the presence of the face straps or adjuncts on the face mask to accept these straps impede a sound grip and contact of the hand with the face mask. Moreover, the grippers are designed to keep the hand away from the strap holders, thus limiting the placement of the gripper(s) and corresponding pressure during operation.

What is therefore needed is a face mask suitable for use with one hand that accommodates the hand in a neutral position while maintaining an adequate seal between the mask and the patient's face.

BRIEF SUMMARY OF THE INVENTION

The present invention provides an asymmetrical face mask suitable for use with one hand that allows an operator to provide a reliable seal with the patient's face with his/her hand in a substantially neutral position.

In one aspect, the invention provides an ergonomic face mask for engaging a patient's face for providing gas to the patient. The mask includes an annular cuff defining an outer periphery of the mask. A dome is attached to the cuff and extends upwardly therefrom. The dome includes a rim asymmetrically positioned on an upper surface of the dome and extending upwardly therefrom. A tubular connector member extends outwardly from the dome for administering the gas.

It is thus one object of the invention to provide an asymmetrical face mask that may be gripped firmly and comfortably with one hand while maintaining an adequate seal with a patient's face.

In another aspect, the dome defines a first groove located to the right of the rim configured to accept the thumb of a human hand. In another aspect, a second groove is located to the left of the rim configured to receive the index finger of a human hand.

It is thus another object of the invention to provide a face mask that is contoured so as to be comfortably gripped by a user's thumb and index finger.

In accordance with another aspect, a concavity is disposed at the distal end of the first groove.

It is thus another object to enable the index finger to have a down-slope orientation during use.

In another aspect, the mask includes a second protuberance disposed radially outwardly with respect to the second groove.

It is thus another object to provide a structure that supports the index finger of the operator in the second groove.

In another aspect, the dome includes a third groove that extends behind the rim.

It is thus another object to provide further support for an operator's hand.

In another aspect, the first, second, and third grooves define a continuous elongated channel.

It is thus another object to provide a continuous groove to define the proper placement of an operator's hand on the mask.

In another aspect, at least a portion of at least one of the three grooves is textured. In a preferred form, the textured surface includes engravings that extend laterally with respect to the channel.

It is thus another object to enhance the gripping ability of the operator.

In another aspect, a third protuberance is disposed behind the rim and configured to provide support the palm of the operator's hand.

It is thus another object to provide further ergonomic support for the operator by providing a support to the palm of the hand.

In accordance with another aspect, a first protuberance is located radially outwardly from the first groove and extends radially outwardly towards an outer periphery of the dome.

It is thus another object to provide a support for the operator's finger to maintain an adequate seal with the patient's face.

In accordance with another aspect, an extended protuberance is disposed at a distal end of the protuberance and extending to a position adjacent the outer periphery of the dome.

It is thus another object to provide an improved seal with the patient's face while maximizing comfort to the operator.

In another aspect, the dome is wider on the left side of the rim than the right side.

It is thus another object to provide an adequate surface area on the dome for the ergonomic placement of the operator's hand.

In another aspect, the cuff is an inflatable cushion configured to provide a seal with the patient's face.

It is thus another object to enable the cuff to fit a variety of facial structures.

In another aspect, a marker is disposed at least partially within the channel to provide an indication as to the proper placement of the operator's hand.

It is thus another object to provide a mask whose use is intuitive to an operator.

These and other aspects of the invention are not intended to define the scope of the invention for which purpose claims are provided. In the following description, reference is made to the accompanying drawings, which form a part hereof, and in which there is shown by way of illustration, and not limitation, preferred embodiments of the invention. Such embodiments do not define the scope of the invention and reference must be made therefore to the claims for this purpose.

BRIEF DESCRIPTION OF THE DRAWINGS

Reference is hereby made to the following figures in which like reference numerals correspond to like elements throughout, and in which.

DETAILED DESCRIPTION OF THE PREFERRED EMBODIMENTS

Figure 2:
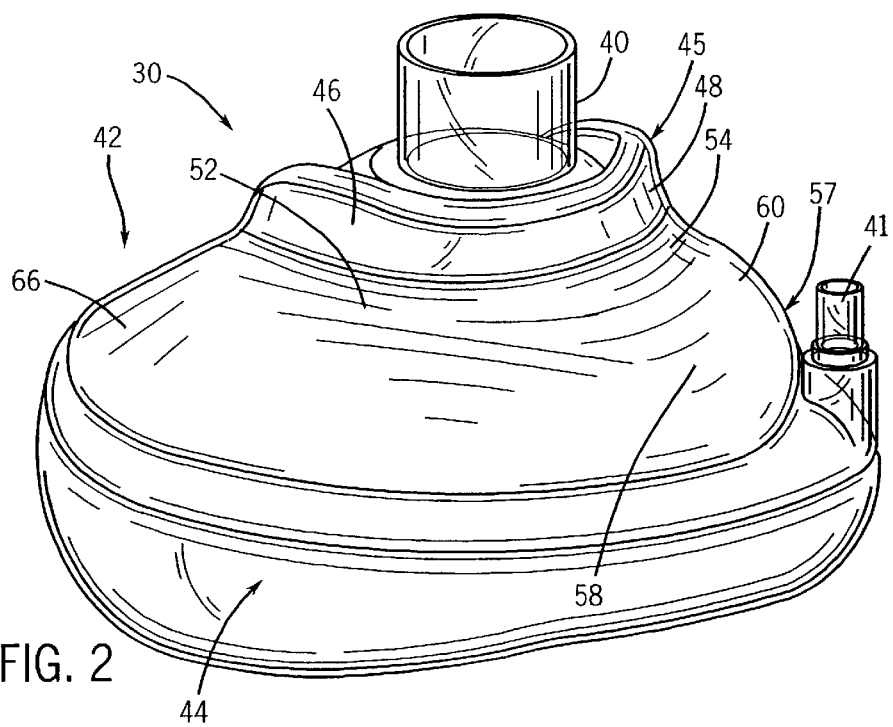
FIG. 2 is a perspective view showing the left side of an ergonomically shaped face mask constructed in accordance with a preferred embodiment of the invention.
Figure 3A:
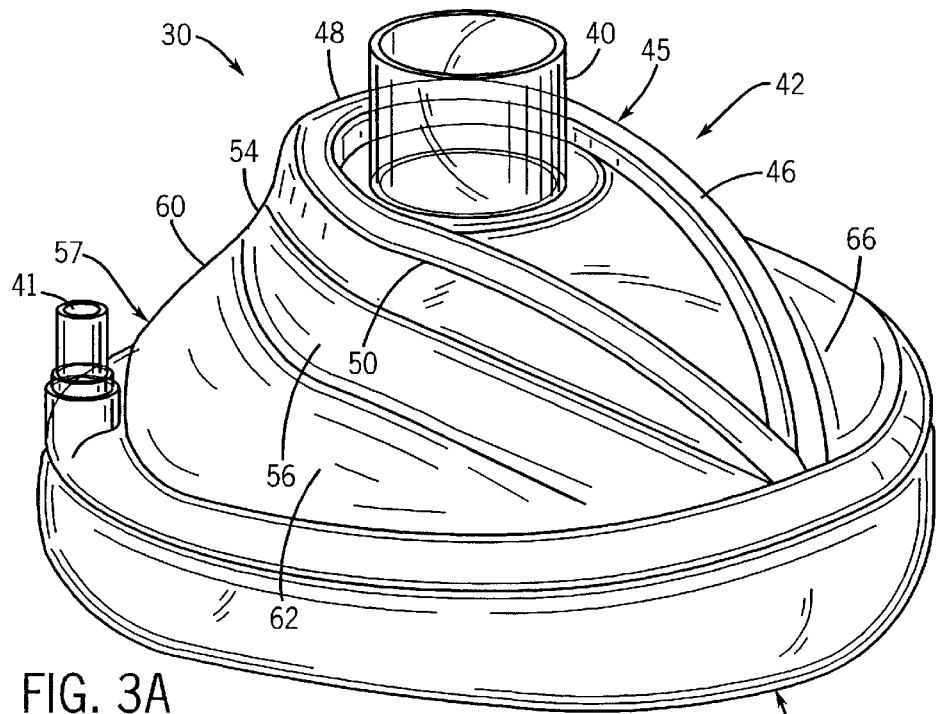
FIG. 3A is a perspective view showing the right side of the ergonomically shaped face mask illustrated in FIG. 2.

Referring now to FIGS. 2 and 3A, an ergonomic face mask 30 includes a cuff 44 at its base that is connected to a dome 42 and a tubular connector member 40 extending outwardly from the dome for administering gas to the patient. The dome 42 defines an outer periphery 37. The mask 30 maybe made of a transparent plastic suitable for a single use, or may alternatively be a rubber or any other material suitable to provide a reusable mask, so long as the mask is sufficiently rigid to allow appropriate manipulation without deformation that would otherwise compromise the seal between the mask and the patient's face. It will be appreciated from the description below that existing molding technology is used for the production of mask 30, thereby enabling mass-production of the mask. The face mask 30 is of the type that engages the face of a patient and receives and delivers oxygen or anesthetic gasses to the patient via connector 40, and is suitable for use with a non-breathing supine patient, or alternatively can be used with spontaneously breathing patients.

The cuff can be configured as an inflatable annular cushion 44 having a port 41 for adjusting the internal pressure to enable the cushion 44 to fit the contour of the patient's face. A skilled artisan appreciates, however, that the cuff could alternatively comprise, for example, a foam or any other material that conforms to a patient's face. Cushion 44 is attached (e.g., glued) to the underside of the outer periphery of dome 42. Advantageously, the dome 42 is asymmetrical when viewed left-to-right to enable the operator to reliably perform the procedure with maximum comfort, as will be described in more detail below.

It should be appreciated from the description below that the terms "front, back, left, and right" are used with reference to a view taken by the operator, with the front being that portion of the mask that engages the patient's chin. The term "radial" is used with respect to connector 40, while the terms "longitudinally" and "laterally" are used with reference to the direction of extension of an operator's fingers during use.

Figure 5:
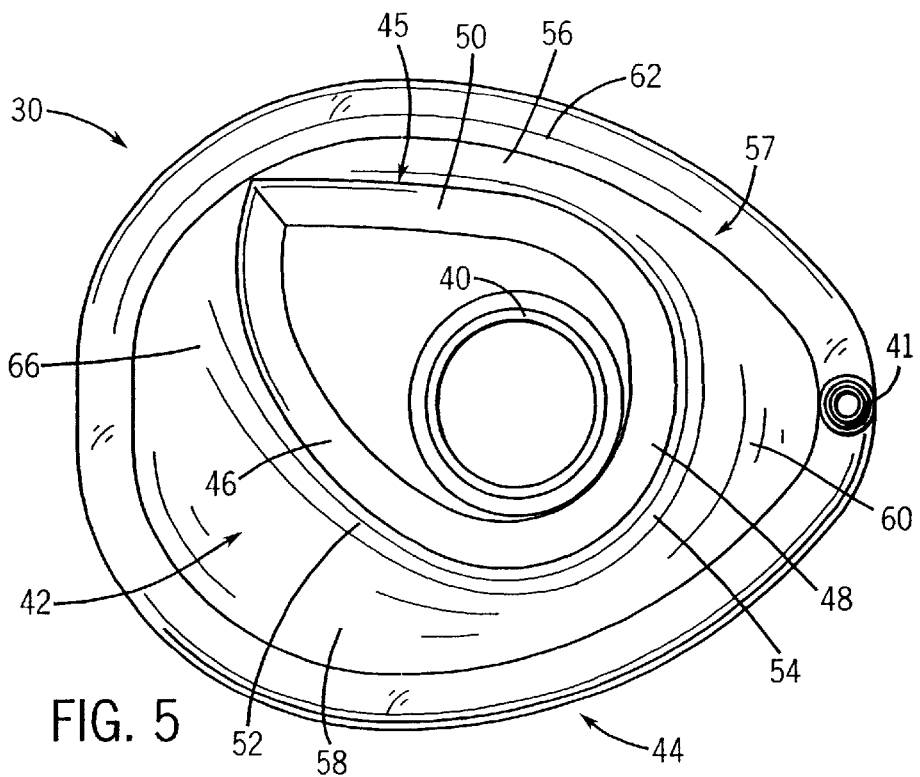
FIG. 5 is a top plan view of the ergonomically shaped face mask illustrated in FIG. 2.
Figure 7A:
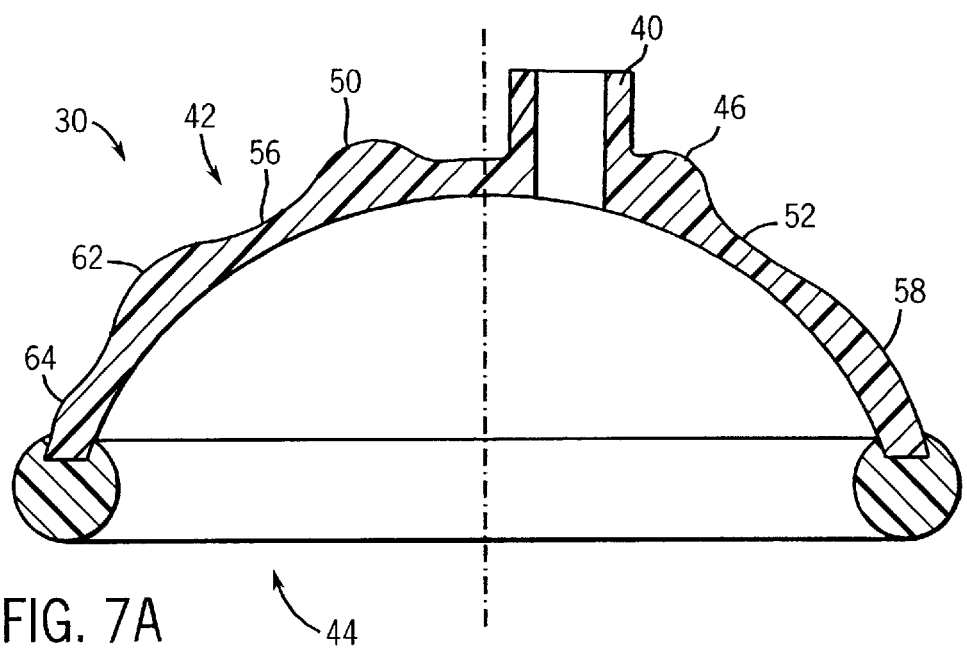
FIG. 7A is a sectional side elevation view of the ergonomically shaped face mask illustrated in FIG. 2.

Referring now also to FIGS. 5 and 7A, the dome 42 includes a rim 45, which is generally a crest-like structure generally resembling the shape of a "teardrop," and a body 57 surrounding the rim and extending downwardly therefrom. The rim 45 is laterally asymmetrically positioned on the dome 42 such that left side of the dome 42 is wider than the right side, and therefore presents a greater upper surface area (e.g., for contact with the hand of an operator), to the left of the rim than to the right of the rim. As such, the face mask 30 may be referred to as an asymmetrical face mask.

Figure 4:
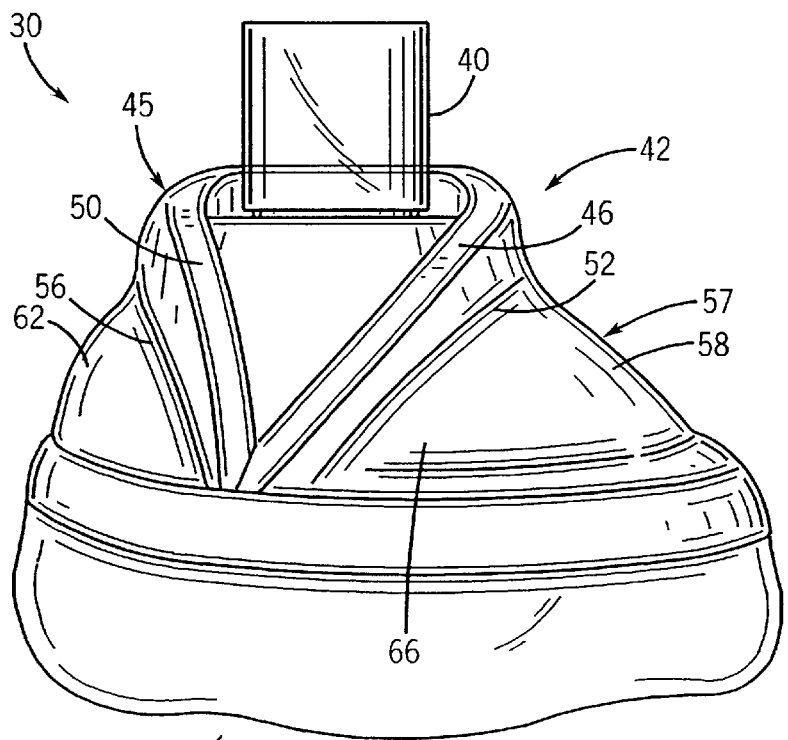
FIG. 4 is a perspective view showing the front of the ergonomically shaped face mask illustrated in FIG. 2.

An anterior concavity 66 is disposed generally at the body 57 and defines the region of lowest height of the dome 42. The rim 45 includes a posterior structure 48 that is located behind the connector 40. The posterior structure 48 defines the highest point of the rim and dome 42. Referring now also to FIG. 4, the rim 45 includes a pair of descending structures that descend from the posterior structure 48 on both sides of the dome 42, encircling the connector 40. In particular, the right descending structure 50 and left descending structure 46 converge to their lowest point on the right anterior part of the dome 42. The left rim 46 is the superior border of the anterior concavity 66. The rim 45 thus has an angulated and asymmetrical aspect and is contoured to fit the left hand of an operator with the hand in a neutral position, as will be described in more detail below.

The dome 42 further defines a depressed channel that surrounds the outer periphery of the rim 45. In particular, the channel includes a right groove 56, a posterior groove 54 and a left groove 52, each of which parallels the rim on the respective side of the dome 42 to define an asymmetrical and continuous concave structure that generally follows the contour of rim 45. The left groove 52 continues anteriorly with the anterior concavity 66.

The dome 42 further includes a plurality of protuberances that surround the grooves 52, 54, and 56 and define convex surfaces on the mask 30. In particular, a right protuberance 62 is disposed adjacent the outer periphery of right groove 56 extends partially along the right side of the mask. A left protuberance 58 is disposed adjacent the outer periphery of left groove 52 and supports the index finger of the operator in groove 52. A posterior protuberance 60 is disposed adjacent the outer periphery of posterior groove 54 and is designed to match the contour of the operator's palm for increased comfort during use. It should be appreciated that the term "protuberance" as used herein refers to a projection of the outer surface of the dome 42. While the protuberances are integrally molded with the dome 42 in accordance with the preferred embodiment, it should be appreciated that they could alternatively be separate members that are attached to the dome.

Figure 3B:
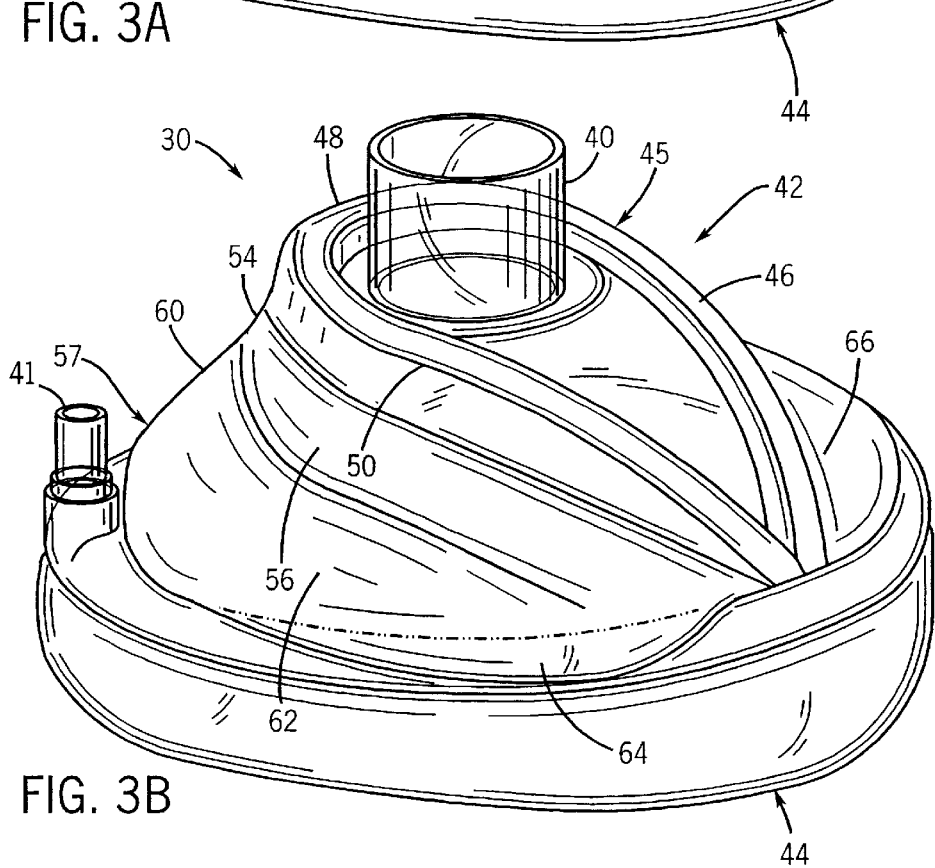
FIG. 3B is a perspective view similar to FIG. 3A, but further illustrating a right dome extension.
Figure 7B:
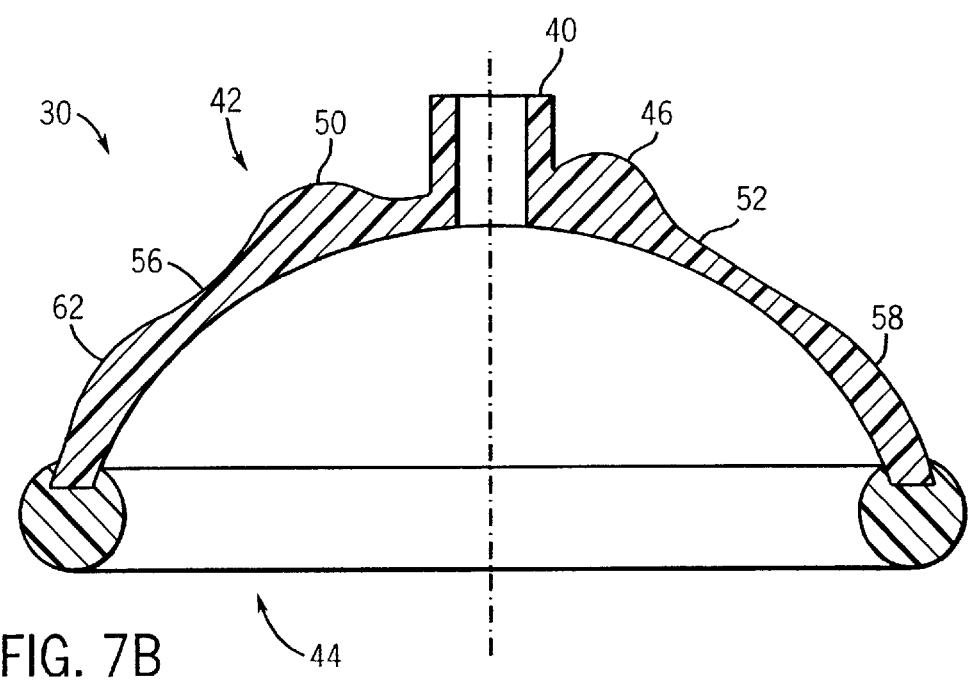
FIG. 7B is a sectional side elevation view of the ergonomically shaped face mask illustrated in FIG. 3B.

Referring now also to FIGS. 3B and 7B, an extension 64 of the right protuberance 62 may extend to the periphery of the right side of the dome 42 (proximal the cushion) to further assist in achieving sufficient pressure on the right side of the patient's face during use. It should thus be appreciated that protuberance 62 and extension 64 not only support the operator's thumb, but also effectively provide an extension to the forces applied by the operator's thumb during use. This further improves the seal with the patient's face at the right side of the mask 30, an area where the seal has been found to fail in conventional symmetrical face masks.

Figure 6:
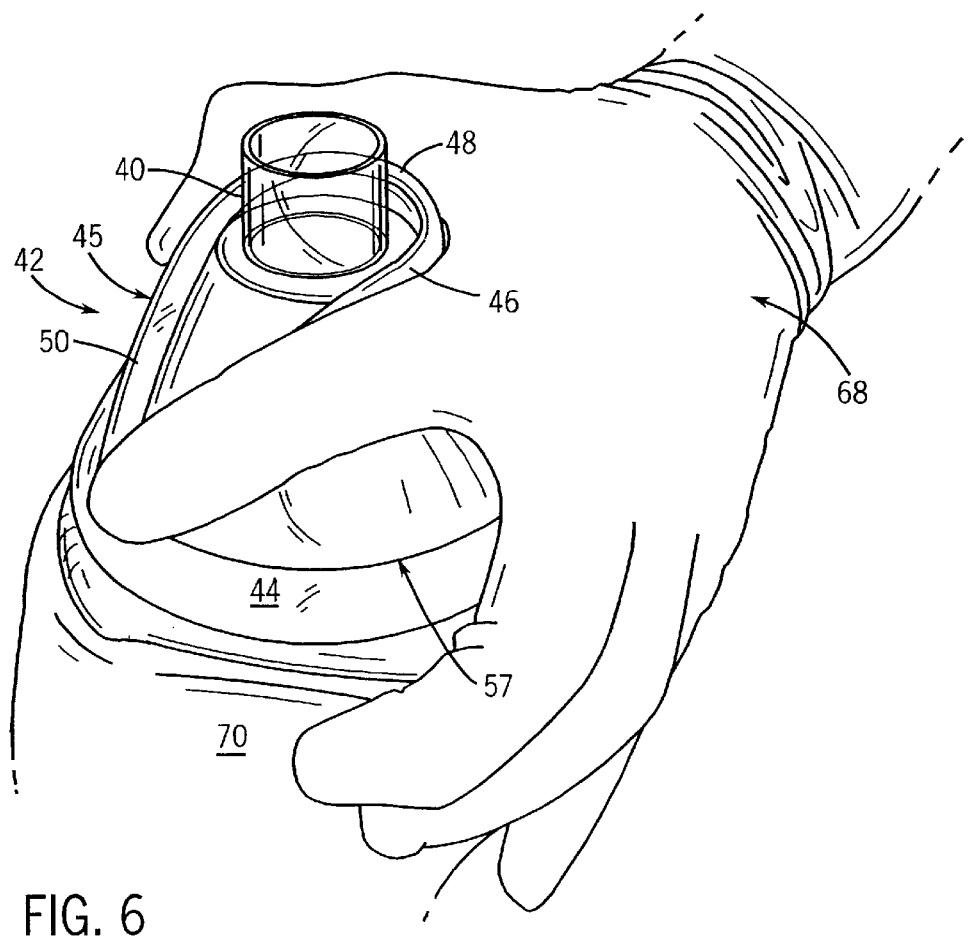
FIG. 6 is a perspective view of the ergonomically shaped face mask illustrated in FIG. 2 showing a left hand placed in a neutral position on the mask while being applied to a patient's face during use.

Referring to FIG. 6, during use, an operator standing behind the patient uses his/her left hand 68 to apply the mask 30 to the face 70 of a supine patient. In particular, the thumb is positioned in the right groove 56 and the index finger in the left groove 52, such that the webbing between the thumb and index finger comfortably fits around and engages the posterior structure 48 of rim 45. The thumb reaches as far as possible on the right side of the mask 30 over the right protuberance 62. Protuberance 62 is positioned such that the thumb in the right groove 56 is capable of optimizing the pressure on the right side of the mask, thus improving the seal of the mask 30 on the patient's face compared to conventional face masks. The pressure on the right side is further assisted by the right extension 64 of the dome 42. The operator has the option of positioning his/her thumb to apply pressure on the right protuberance 62 (to improve the pressure on the right side) or on the right rim 50 (to increase the grip on the mask). This increases the versatility of the mask and will improve the seal on the right side of the patient's face, where conventional symmetrical face masks have been known to fail.

Advantageously, the asymmetry of the mask 30 resides in the fact that the left side of the dome 42 is wider than the right side of the dome. As a result, the force exerted onto the mask by the thumb is distributed across a smaller surface area, thereby achieving a greater pressure than possible in conventional symmetrical masks. The increased pressure on the right side of the patient's face 70 contributes to an enhanced seal compared to prior art face masks. Furthermore, the wider left side of the dome 42 enables the comfortable positioning of the fingers of the left hand on the mask 30 and the ability to perform a jaw thrust with the hand in essentially a neutral position.

The index finger is positioned in the left groove 52, and follows along the contour of the left groove. The tip of the index finger will thus be placed at the lowest point of the mask 30, the anterior concavity 66, such that the finger has a down-slope orientation and reaches around on the right side of the mask 30 during use. As a result, the index finger presses the mask 30 against on the right anterior margin of the dome to help seal the right side of the mask against the patient's face. The index finger uses the left rim 46 to optimize the grip and the anterior concavity 66 to improve the seal on the right side.

The palm of the left hand 68 is in contact with the posterior portion of the dome 42 and, in particular, applies pressure naturally over the left protuberance 58 and the posterior protuberance 60. It is thus appreciated that the protuberances are designed to accommodate the hand in a neutral position and to allow the hand to apply proper "upper" pressure on the mask. When the hand is in a neutral position, the wrist and forearm of the operator are relatively straight and not twisted or otherwise contorted. Furthermore, the thumb of the operator is positioned higher than the rest of the fingers. It is further appreciated that the angulation of the mask, in which the posterior end is higher than the anterior end, places the palm in an ergonomically higher position than the fingers.

The middle, ring, and small fingers thus fall naturally in a relaxed position on the left side of the mask. Advantageously, the strength and comfort of these fingers are increased due to this ergonomic position of the hand. For example, each finger is in full contact with the mask with the hand in a neutral position with the palm of the hand in an elevated position with respect to the fingers. The rim 45 does not point to the tip of the patient's jaw, but rather points towards the right side of the patient's jaw, thereby enabling the middle, ring, and small fingers of the operator to engage the left side of the patient's jaw. Accordingly, the position of these fingers is optimal to pull the mask in the face of the patient, to lift the chin of the patient, and perform the "jaw thrust" maneuver. These maneuvers are critical when it is necessary open the patient's airway that may be obstructed, for example, by a fallen tongue or soft tissue.

Figure 1:
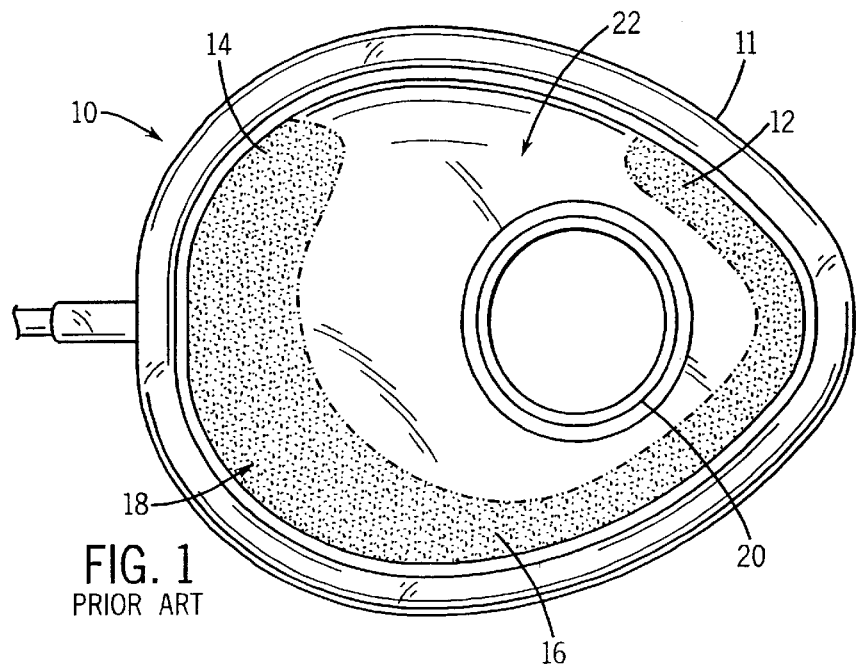
FIG. 1 is a top plan view of a conventional symmetrical face mask showing the asymmetrical pressure area developed by the left hand during use.

Conventional face masks, such as that illustrated in FIG. 1, ignore the fact that some operators will have larger or smaller hands than others. In particular, various cuff sizes (e.g., small, medium, and large) are necessary depending on the distance between the nasal bridge and the chin groove of the patient. Because the domes of conventional face masks are designed to accommodate the cuff size, the domes have been proportional to the size of the cuff, thereby ignoring the difficulties experienced by, for example, an operator with small hands administering ventilation to a patient that requires a large mask. This could result in discomfort to the user and could further compromise the seal between the mask and the patient's face. Advantageously, the present invention recognizes that the dome 42 and the corresponding structures thereon, in particular those that engage the operator's hand, may be provided in multiple sizes for each given cuff size. As a result, the operator will be able to comfortably administer ventilation to a patient regardless of the size of the patient's face while providing an adequate seal.

Figure 8A:
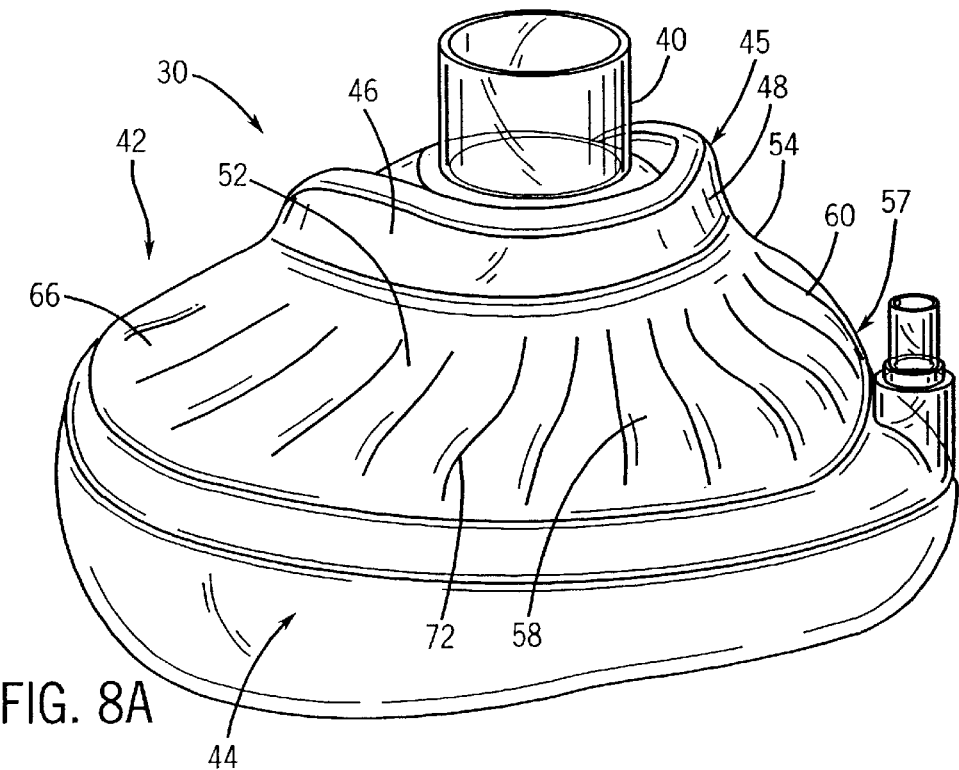
FIG. 8A is a perspective view of the left side of an ergonomically shaped face mask having engravings in accordance with an alternate embodiment of the invention.
Figure 8B:
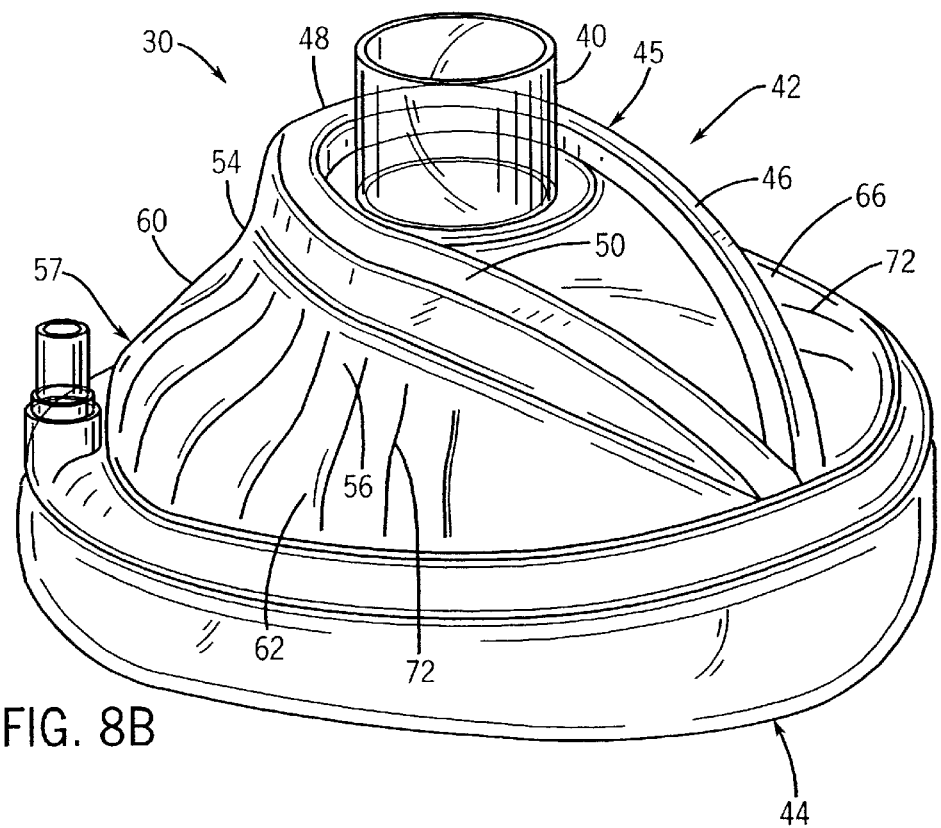
FIG. 8B is a perspective view of the right side of the ergonomically shaped face mask illustrated in FIG. 8A.

Referring now to FIGS. 8A and 8B, the outer surface of dome 42 may be textured in accordance with an alternate embodiment of the invention. In particular, engravings 72 may be formed onto the mask 30 so as to extend into the grooves 52–56 in a direction transverse to the direction of extension of each respective groove so as to further prevent the operator's hand from slipping during use. The engravings 72 further optimize hand placement by more clearly defining the grip area and increase adherence between the hand and the mask such that the operator will not need to reposition his/her hand when the mask is initially gripped. The engravings 72 are particularly preferable when the operator administers ventilation using a smooth gloved hand.

Figure 9:
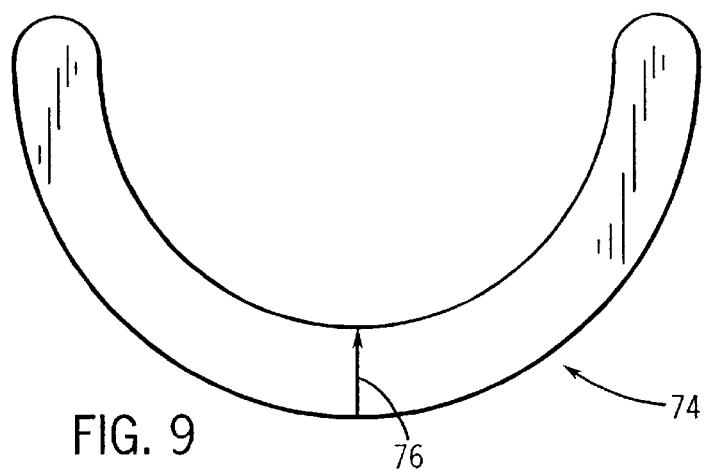
FIG. 9 shows a model of a marker in the form of an adherent sticker attachable to an ergonomically shaped face mask constructed in accordance with the present invention.

Referring to FIG. 9, the grip area may be more clearly designated and the adherence between the hand and mask may be further enhanced through the implementation of a marker, such as sticker 74, that may additionally be attached to the mask 30. The sticker 74 is sized such to be properly positioned in the posterior groove 54 and left groove 52 when arrow 76 points towards the middle of the left side of the connector 40. It should be easily appreciated, however, that the sticker 74 may assume other configurations. For example, the sticker could also extend into the right groove 56 to provide an enhanced gripping surface for the operator's thumb. It should be appreciated that various size stickers are available to properly correspond to the size of the mask.

Sticker 74 is preferably transparent to enable the clinical observation of the patient by the operator during use. The inner surface of the sticker 74 is highly adhesive to ensure that the sticker will remain in its proper position during use. The outer surface 78 may be textured and adherent to provide an enhanced gripping surface. In addition to assisting the experienced anesthesiologist, the sticker 74 could additionally be used to train inexperienced users in properly operating the mask 30. It should further be appreciated that such a sticker could also be implemented with conventional symmetrical masks 10 of the type illustrated in FIG. 1 to identify the proper gripping area. It should be further appreciated that while a sticker is described in accordance with a preferred embodiment, the marker could alternatively assume other forms that provide the advantages discussed above. For example, the markings could be molded or otherwise fabricated integrally with the dome 42 to indicate the proper positioning of the user's hand.

Mask 30 could further be provided with strap hooks (not shown) that would attach to the dome to enable straps to extend around the patient's head and aid in securing the cuff 44 to the patient's face as understood by one having ordinary skill in the art.

It should thus be appreciated that the face mask 30 is designed to be gripped such that sufficient lower pressure and upper pressure are inherently achieved along with the ability to perform an adequate jaw thrust when the mask is gripped properly. Advantageously, dome 42 is designed such that proper position of the operator's hand is intuitive. Because the operator's left hand is in a neutral, uncontorted, position during use, carpal tunnel pressure experienced by the operator is also minimized. Advantageously, the entire operation of mask 30 may be performed by a single operator with one hand (i.e. the left hand) in an ergonomic position such that the other hand may be used to provide gas to the patient under positive pressure. Because an adequate seal between the mask and patient thus is realized while maintaining maximum comfort, the operator will not need to change his/her grip during use. This improves oxygenation of the patient and reduces pollution of the operating room with anesthetic gasses while reducing unnecessary fatigue to the operator.

The present invention should not be interpreted as an endorsement to ignore the two-hand technique recommended by the "Basic Life Support (BLS) for Health Care Providers" and the "Guidelines 2000 for Cardiopulmonary Resuscitation—CPR and Emergency Cardiovascular Care."

To this end, it should be appreciated that the mask 30 may alternatively be applied to a patient by a single operator using two hands. However, when a rescuer is forced, due to certain circumstances, to control both the mask 30 and bag containing the gas, he/she will be able to provide a seal with the patient's face with one hand having while achieving an improved seal and greater comfort over conventional face masks. The other hand will then be free to attend to the providing positive pressure to the mask by squeezing the bag (not shown).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements included within the spirit and scope of the invention, as set forth by the appended claims.

I claim:

1. An ergonomic positive pressure face mask for engaging a patient's face for providing gas to the patient, the mask comprising:

(A) a cuff defining an outer periphery of the mask;
 (B) a dome attached to the cuff and extending upwardly therefrom, for receiving positive pressure, wherein the cuff is configured to provide a substantially air-tight seal with the patient's face upon application of positive pressure to the dome;
 (C) an ergonomic rim connected to the dome such that the rim is left-right asymmetrically positioned with respect to the mask, wherein the rim may be engaged to apply positive pressure to the dome; and
 (D) a tubular connector member extending outwardly from the dome for administering the gas.

2. The mask as recited in claim 1, wherein the dome defines a first groove located to the right of the rim configured to receive the thumb of a human hand.

3. The mask as recited in claim 2, wherein the dome further defines a second groove located to the left of the rim configured to receive an index finger of a human hand, respectively.

4. The mask as recited in claim 3, further comprising a concavity disposed at a distal end of the second groove.

5. The mask as recited in claim 3, wherein the second groove has a down-slope orientation.

6. The mask as recited in claim 3, further comprising a protuberance disposed radially outwardly with respect to the second groove.

7. The mask as recited in claim 3, wherein the dome further defines a third groove extending behind the rim.

8. The mask as recited in claim 7, wherein the first, second, and third grooves define a continuous elongated channel.

9. The mask as recited in claim 8, wherein at least a portion of the surface of the channel is textured.

10. The mask as recited in claim 9, wherein the textured surface comprises engravings that extend laterally with respect to the channel.

11. The mask as recited in claim 8, wherein a marker is disposed at least partially within the channel to provide an indication as to a proper placement of the operator's hand during use.

12. The mask as recited in claim 1, wherein the dome further comprises a first protuberance located radially outwardly from the first groove and extending radially outwardly towards an outer periphery of the dome.

13. The mask as recited in claim 12, further comprising an extended protuberance disposed at a distal end of the first protuberance and extending to a position adjacent the outer periphery of the dome.

14. The mask as recited in claim 1, further comprising a protuberance disposed behind the rim and configured to provide support the palm of an operator's hand.

15. The mask as recited in claim 1, wherein the dome is wider on the left side of the rim than on the right side of the rim.

16. The mask as recited in claim 1, wherein the cuff comprises an inflatable cushion configured to provide a seal with the patient's face.

17. The mask as recited in claim 1, wherein the rim substantially resembles the shape of a teardrop.

18. The mask as recited in claim 1, wherein the rim is left-right asymmetrically positioned on the dome.

19. An ergonomic positive pressure face mask for engaging a patient's face for providing gas to the patient, the mask comprising:

(A) a cuff defining an outer periphery of the mask;

(B) an asymmetrical dome attached to the cuff and extending upwardly therefrom for receiving positive pressure, wherein the cuff is configured to provide a substantially air-tight seal with the patient's face upon application of positive pressure to the dome, and wherein the dome defines a left region, a right region opposite the left region, an anterior region, and a posterior region opposite the anterior region, the dome including:

i. a first protuberance located at the right region that projects outwardly from the dome to define a corresponding first convex surface on the dome;

ii. a second protuberance located at the left region that projects outwardly from the dome to define a corresponding second convex surface on the dome; and iii. a third protuberance located at the posterior region that projects outwardly from the dome to define a corresponding third convex surface on the dome;

(C) a rim connected to the dome that defines a groove at an interface between the rim and the dome; and (D) a tubular connector member extending outwardly from the dome for administering the gas, wherein the first, second and third protuberances and the groove are adapted to be engaged by a single hand of a user applying positive pressure to the dome.

20. The face mask as recited in claim 19, wherein the first protuberance extends to a location proximal the cuff at the right region.

* * * * *